(12) United States Patent
Choate et al.

(10) Patent No.: US 7,015,028 B2
(45) Date of Patent: Mar. 21, 2006

(54) PROCESS FOR TREATMENT OF ORGANIC WASTE MATERIALS

(75) Inventors: Chris E. Choate, Discovery Bay, CA (US); Paul A. Sherman, Petaluma, CA (US); Ruihong Zhang, Davis, CA (US)

(73) Assignee: Alta Environmental Services, Inc., Dixon, CA (US)

( * ) Notice: Subject to any disclaimer, the term of this patent is extended or adjusted under 35 U.S.C. 154(b) by 0 days.

(21) Appl. No.: 10/427,454

(22) Filed: Apr. 30, 2003

(65) Prior Publication Data

US 2004/0219650 A1 Nov. 4, 2004

(51) Int. Cl.
*B09B 3/00* (2006.01)
*B01D 1/00* (2006.01)
*C02F 1/00* (2006.01)
*C12M 1/00* (2006.01)
*C12M 3/00* (2006.01)

(52) U.S. Cl. ............................... 435/262.5; 210/512.1; 210/600; 435/289.1

(58) Field of Classification Search ............ 435/262.5, 435/283.1, 298.1, 289.1; 210/600, 767, 800, 210/512.1, 542
See application file for complete search history.

(56) References Cited

U.S. PATENT DOCUMENTS

| | | | |
|---|---|---|---|
| 3,984,484 A * | 10/1976 | Scremin et al. ............ 568/749 |
| 4,632,692 A * | 12/1986 | Lebesgue et al. ............ 71/10 |
| 5,461,843 A | 10/1995 | Garvin et al. |
| 5,500,306 A * | 3/1996 | Hsu et al. ................... 429/17 |
| 5,566,532 A | 10/1996 | Inman et al. |
| 5,724,793 A | 3/1998 | Inman et al. |
| 5,782,950 A * | 7/1998 | Kanitz et al. ................. 71/10 |
| 6,062,004 A | 5/2000 | Inman et al. |
| 6,202,389 B1 | 3/2001 | Inman et al. |
| 6,240,980 B1 | 6/2001 | Inman et al. |
| 6,342,378 B1 | 1/2002 | Zhang et al. |
| 6,516,590 B1 | 2/2003 | Inman et al. |
| 6,709,500 B1 * | 3/2004 | West ......................... 96/216 |

FOREIGN PATENT DOCUMENTS

WO WO 02/062497 A1 8/2002

OTHER PUBLICATIONS

U.S. Appl. No. 11/031,218, Organic Waste Material Treatment System, filed Jan. 6, 2005, Chris E. Choate.

* cited by examiner

*Primary Examiner*—David M. Naff
*Assistant Examiner*—Deborah K. Ware
(74) *Attorney, Agent, or Firm*—Carr & Ferrell LLP

(57) ABSTRACT

A multi-stage process and system for treating organic waste materials includes steps of hydrolyzing the materials in an anaerobic vessel, transferring the liquid product of hydrolysis to an anaerobic digester, and further decomposing the waste materials under aerobic conditions to yield a compost product usable as a soil amendment. Biogas produced by digestion of the hydrolysis liquid product may be burned to generate electricity or heat, and the liquid digester product may be recirculated for use as an inoculant to aid hydrolysis of subsequently processed batches of waste materials.

22 Claims, 4 Drawing Sheets

PROCESS FOR TREATMENT OF ORGANIC WASTE MATERIALS

BACKGROUND

1. Field of the Invention

The present invention relates generally to processing of waste materials, and more particularly to processes and systems for treating organic waste materials to form a compost product.

2. Description of the Prior Art

Anaerobic digestion and composting processes have co-existed for many years as disposal alternatives for organic waste materials. Such materials include agricultural materials, "green" wastes, and pre- and post-consumer wastes. The primary objective of anaerobic digestion is the production of a mixture of hydrocarbon gases ("biogas"), which may be utilized as an energy source to generate electricity and/or heat. Any solid material remaining at the completion of the anaerobic digestion process is typically disposed of by conventional methods, such as transferring the material to a landfill. In contrast, composting processes focus on the production of a solid product that may be employed as a soil amendment.

Because of the high capital costs associated with anaerobic digestion equipment, composting has become the dominant method in the United States for the management and re-use of organic waste materials generated in rural and suburban settings. The growing use of composting as a preferred alternative to disposal of organic waste material has made some common environmental problems apparent. These problems include emissions of noxious gases and ozone pre-cursors, runoff from the compost facility, and high energy consumption during material processing. These problems may become particularly acute if the organic waste material contains large amounts of food waste or other high moisture content waste. Commercial-scale composting is also subject to a variety of financial considerations, including capital investment related to accommodating peak seasonal feedstock deliveries, compost process time, and controlling the timing of compost production to match the seasonal demand of the agricultural industry and other compost buyers.

It is therefore an objective of the invention to provide a process and system for treating organic waste materials that avoids or reduces the aforementioned environmental problems and addresses the financial considerations in an economically advantageous manner.

SUMMARY

In a preferred embodiment of the invention, organic waste materials are treated via a multi-stage process involving anaerobic hydrolysis, anaerobic digestion of the liquid hydrolysis product, and aerobic composting of the solids remaining after hydrolysis. The organic waste materials may be pre-treated by adding a amount of liquid inoculant sufficient to raise the moisture content of the organic waste to a minimum of sixty percent. The organic waste material is then placed within a sealed hydrolysis vessel, which may take the form of a cylindrical polymer bag. Hydrolysis of the organic matter within the vessel results in the production of a liquid product, which is removed from the vessel via a conduit that communicates with the vessel's interior. Removal of the liquid may be performed either continuously, at specified intervals, or at the completion of the hydrolysis process.

The liquid hydrolysis product transferred from the vessel, which may be temporarily stored in a holding tank, is passed to a conventional anaerobic digester. In a thermophilic digester, methanogenic bacteria convert organic matter that is dissolved and/or suspended in the liquid hydrolysis product to a biogas product. The biogas product may be combusted prior to release to the atmosphere in order to eliminate or reduce emissions of flammable or otherwise objectionable gaseous species, such as methane. Thermal energy produced by combustion of the biogas may be utilized to supply heat and/or electrical power for processing operations. The liquid digester product remaining after completion of the digestion process may be removed from the digester and employed as inoculant for hydrolysis of subsequently processed organic waste material.

After completion of hydrolysis, the remaining solid waste material may be removed from the vessel and composted under aerobic conditions. The composting process may be implemented as a static reversed air aerobic composting system, wherein the solid waste material is placed in a pile atop a pad adapted with an array of ports that communicate with a manifold. A blower, coupled to the manifold, draws ambient air through the solid waste material and into the ports and manifold. The ambient air drawn through the pile and into the manifold is passed through a biofilter to remove undesirable species before discharge to the atmosphere. Alternatively, after completion of hydrolysis, the remaining solid waste material may be composted using an aerobic windrow process, positive or negative aerated static pile or other suitable process. The end result of the composting process is a decomposed material that may be used as a soil amendment.

The foregoing waste material treatment process present several advantages over prior art techniques, including the reduction of emissions of ozone precursors and other noxious or otherwise objectionable gases (by removal of such species during the hydrolysis process), lowering the net energy requirements associated with the composting process (since energy required for material processing is offset by energy produced by utilization of the biogas product), and the ability to rapidly and inexpensively scale the process to meet peak throughput demands by adjusting the number and capacity of the relatively low-cost hydrolysis vessels.

DETAILED DESCRIPTION

Figure 1:
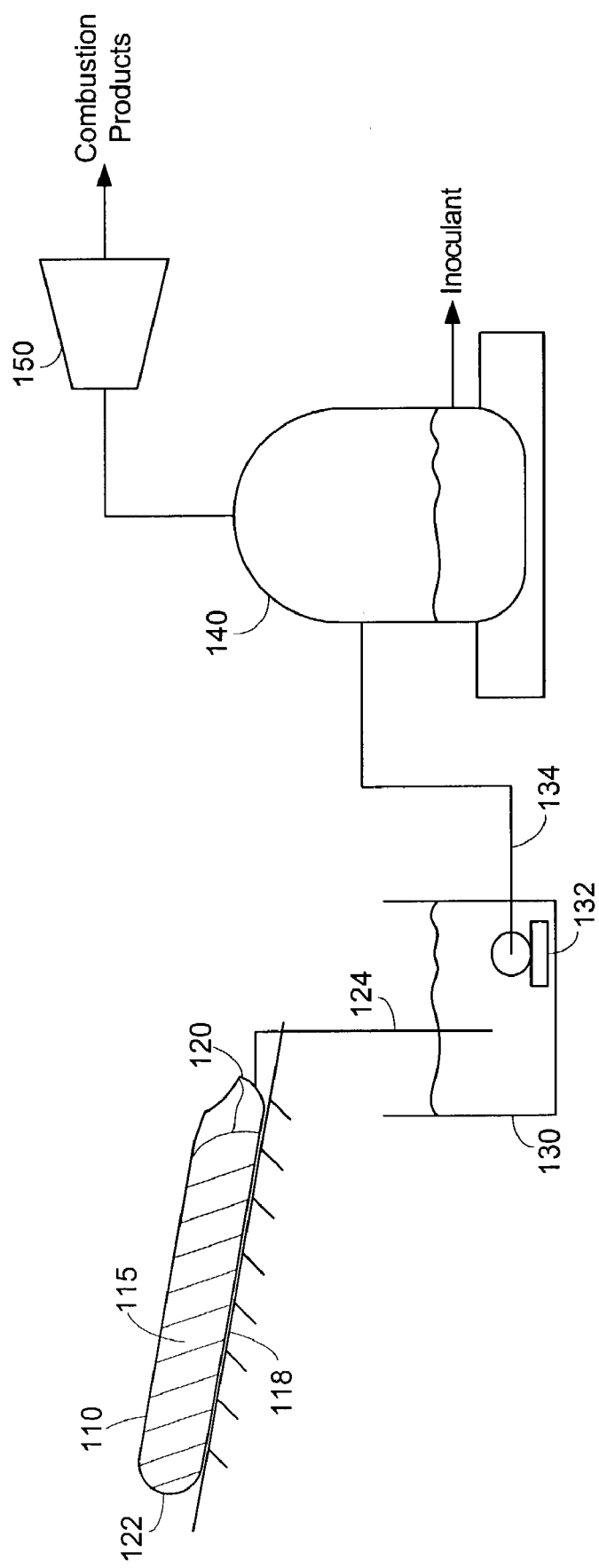
FIG. 1 is a symbolic diagram of an organic waste treatment system in accordance with an embodiment of the invention.

FIG. 1 symbolically depicts the major components of an organic waste treatment system 100 implemented in accordance with an exemplary embodiment of the invention. A flexible hydrolysis vessel 110 contains a volume of organic waste material 115 having relatively high moisture content and density. The hydrolysis vessel 110 has pliable walls formed from a polymer or other material that is substantially impermeable to gases and liquids. The ends of vessel 110 are closed and sealed to provide an anaerobic environment for the hydrolysis of the organic waste material 115. Details regarding the construction of vessel 100 are set forth below in connection with FIG. 2.

The vessel 100 rests on a supporting surface 118, which is sloped along the longitudinal axis of vessel 110 such that the bottom portion of a first end 120 of the vessel 110 is situated lower than the bottom portion of the opposite end 122 of the vessel 110. This condition causes liquids produced during anaerobic hydrolysis of organic waste 115 to flow under the influence of gravity to a region of the vessel interior proximal to first end 120. As is described below in connection with FIG. 2, liquid flow within vessel 110 may be facilitated by placement of one or more perforated pipe structures within the vessel 110. In one embodiment, the supporting surface 118 is a heated supporting surface.

At the completion of the anaerobic hydrolysis process, or at specified intervals during the anaerobic hydrolysis process, collected liquid (including dissolved and suspended organic compounds) is removed from the interior of the vessel 110 via conduit 124. The conduit 124 may comprise pipe formed from PVC or other suitable material that is resistant to attack by organic acids and other corrosive compounds contained within the hydrolysis liquids. A normally-closed valve (not shown in FIG. 1) integrated with or located exterior to vessel 110, may be opened to effect flow of the collected liquid out of the vessel. The liquid flows through conduit 124 and into a holding tank 130. The holding tank 130 serves as a reservoir to store liquid produced during anaerobic hydrolysis of the waste material until digester 140 is available for further processing of the liquid. When digester 140 becomes available, a suitable quantity of liquid is pumped by pump 132 from the holding tank 130 through line 134 into the interior of the digester 140.

The digester 140 may be in the form of a conventional closed digester vessel in which the hydrolysis liquid product is combined with methane producing bacteria and incubated for a predetermined period to produce biogas and a liquid digester product. The interior of digester 140 may be conventionally adapted with membranes, heaters, and other structures, as appropriate, to facilitate and optimize the digestion process. Digesters of this general description are available from industrial suppliers such as Onsite Power Systems, Inc. of Camarillo, Calif. The biogas is preferably combusted prior to release to the atmosphere to destroy methane (a primary component of the biogas) and other flammable, noxious, and other species for which emission to the environment is undesirable, dangerous, and/or regulated. Thermal energy produced by combustion of the biogas may be utilized for various purposes, including generation of electrical power, which may in turn be used to drive various components of the waste treatment system 100, including blowers and pumps. An electrical generator 150 (which may comprise, for example, a conventional turbine generator or microturbine) may be provided in the FIG. 1 system for this purpose. Alternatively and/or additionally, hot exhaust gases resulting from biogas combustion may be passed through a heat exchanger to produce heated air and/or liquid streams for use in the digester 140 or other components of the waste treatment system 100 or related apparatus. The exhaust gases from biogas combustion may be subjected to filtration and/or other pollutant control processes, as appropriate, prior to atmospheric venting. In yet another alternative embodiment, the biogas is processed and refrigerated to produce liquid natural gas (LNG), which may be stored or shipped offsite for use as an energy source.

While the system 100 is depicted as having a single hydrolysis vessel 110 and digester 140, those skilled in the art will recognize that commercial implementations may include any number of hydrolysis vessels and digesters, as suited to a specific application and required throughput. Multiple hydrolysis vessels and/or digesters may be arranged and linked in any suitable arrangement. For example, multiple hydrolysis vessels may be arranged in parallel to supply liquid to a single holding tank and digester. Alternatively, multiple hydrolysis vessels may be coupled to a plurality of digesters, each of which may be brought on-line or off-line as appropriate according to throughput and maintenance requirements.

Figure 2:
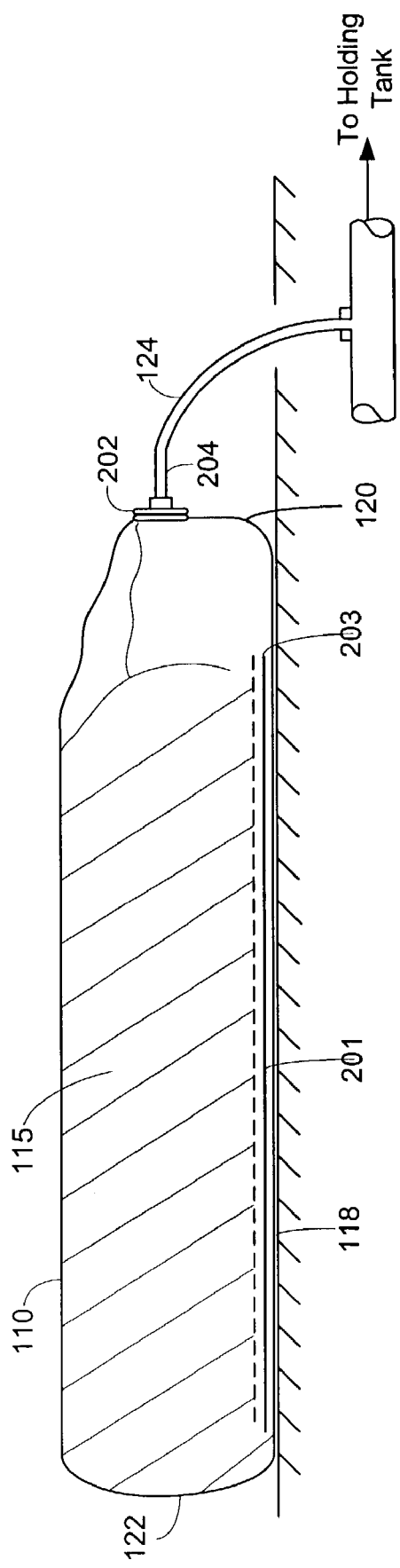
FIG. 2 is a symbolic longitudinal cross-sectional view of the flexible hydrolysis vessel of the FIG. 1 system.

FIG. 2 is a longitudinal cross-sectional view depicting anaerobic hydrolysis vessel 110. The vessel 110 may take the form of an elongated, generally cylindrical container having thin walls formed from a polymer material. Desirable properties of the polymer material include impermeability to gases and liquids, high resilience (to avoid tearing), and high resistance to chemical attack from organic acids and other compounds formed during hydrolysis. Containers of this general description are available from commercial suppliers such as Ag-Bag International Limited of Warrenton, Oreg. The dimensions of the vessel 110 may be selected in view of the required throughput, structural integrity, and space considerations. In an exemplary commercial implementation, vessel 110 has a diameter of approximately five to ten feet, and a length in the range of 100–200 feet.

In the foregoing implementation, at least one end of the vessel 110 will initially be open to enable placement of the organic waste material 115 into the vessel 110. As is described below in connection with FIG. 3, filling of vessel 110 may be accomplished by using a conventional bagging machine.

A perforated drainage pipe 201 may be placed within the interior of vessel 110 to facilitate the flow of liquids generated during the hydrolysis process to the first (lower) end of the vessel. Pipe 201 is located at or near the bottom portion of the interior and traverses the length of the vessel. Liquids enter pipe 201 through holes in the pipe wall and exit the pipe at a mouth 203 opening to the unfilled region of the vessel adjacent to the vessel's lower end. Placement of perforated pipe 201 within the vessel may be accomplished by employing an apparatus and method substantially similar to that described in U.S. Pat. No. 5,461,843 ("Method for Treatment of Bagged Organic Materials" by Garvin et al.).

Vessel 110 is adapted with a port 202 located proximal to the first (lower) end 120 to enable removal of hydrolysis liquid product. The port 202 is coupleable to conduit 124 by a flange 204 such that accumulated liquids flow into conduit 124 and thereafter into holding tank 130. Vessel 110 may be continuously coupled to conduit 124 throughout the hydrolysis stage; alternatively, conduit 124 may be coupled to vessel 110 only when drainage of the hydrolysis liquid is desired (such as at periodic intervals during or at the completion of the hydrolysis process). One or more valve structures, which may be integrated with port 202 or located externally thereto, are provided to selectively inhibit or allow the flow of hydrolysis liquids into conduit 124 while preventing the ingress of air and thereby maintaining the anaerobic conditions within the vessel.

Figure 3:
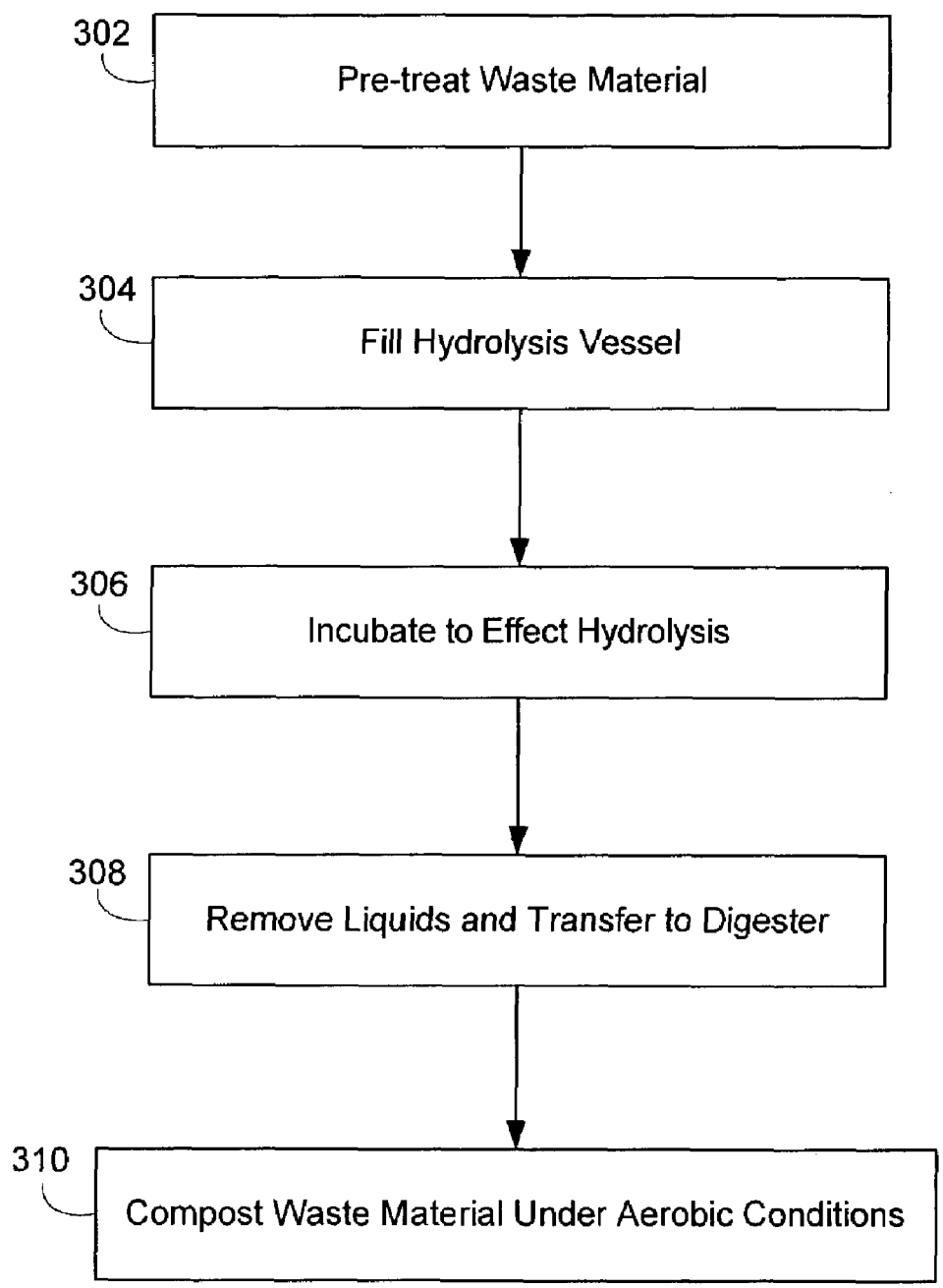
FIG. 3 is a flowchart depicting process steps for treating organic waste material, in accordance with an embodiment of the invention.

FIG. 3 depicts the process steps for treating organic waste material in accordance with an embodiment of the invention. The process 300 will be described in terms of its application to exemplary waste treatment system 100; however, the process should not be construed as being limited to implementation in the FIG. 1 system. In step 302, the organic waste material is pre-treated prior to placement within the vessel 110. In a typical commercial composting facility, the organic waste material comprises multiple waste streams, including without limitation agricultural waste, food waste, residential lawn/garden waste, and cannery waste. The pre-treatment step 302 may include blending of two or more of these waste streams. The blending proportions (percentages of each waste stream in the organic waste material) may be adjusted to optimize various properties of the organic waste material, such as carbon:nitrogen ratio. The blended material may then be ground to reduce the average particle size and increase surface area available for reaction. According to one implementation, the waste material is ground to a maximum particle size (longest dimension) of 1.5 inches.

The pre-treatment step 302 may further include the addition of a liquid inoculant to the organic waste material 115. The addition of inoculant supplies the moisture and anaerobic bacteria required for the hydrolysis reactions to occur. Inoculant is available in bulk from commercial suppliers; however, according to a preferred implementation, the inoculant is wholly or partially comprised of the liquid digester product produced by digestion of a previously processed batch of organic waste material 115. Use of the liquid digester product as the inoculant confers a substantial economic benefit by removing the need to purchase commercial inoculant and avoiding costs associated with disposal/treatment of the liquid digester product. The amount of inoculant added to the organic waste material 115 should be sufficient to raise the moisture content to at least (and preferably significantly greater than) sixty percent by weight. The resultant organic waste material 115 will typically have a density of approximately 800–1000 pounds/cubic yard.

Next, in step 304, the pretreated organic waste material 115 is placed within the vessel 110. According to one implementation, placing the organic waste material 115 in the vessel 110 includes placing the vessel 110 on a supporting surface 118 that is heated. Placement of the organic waste material 115 within the vessel 110 may be achieved by employing a bagging machine of the type described in U.S. Pat. No. 5,566,532 and sold by Ag-Bag International Limited. Generally, such machines include a conveyor for transferring material from a hopper into a feed tunnel, and a rotor for compressing the material and propelling the compressed material into an elongated bag having an open end thereof affixed to the tunnel exit. A bagging machine may further include a ram removably received within the interior of vessel 110 for urging the material along the length of the vessel. As is depicted in FIG. 2, the entire interior volume of vessel 110 is filled with organic waste material 115 except for a region adjacent to first (lower) end 120, which is left unfilled to accommodate liquid product generated during hydrolysis of the organic waste material 115. In a typical implementation utilizing a vessel 110 having a length of 200 feet, the unfilled region will have a length of approximately 10 feet. The vessel 110 is sealed at the completion of the placement step to create an anaerobic environment for hydrolysis of the organic waste material 115. Prior to sealing, air remaining in the vessel 110 (e.g., bag) may be pumped out using a vacuum pump in order to reduce the oxygen concentration within the vessel 110.

The organic waste material 115 is then incubated within sealed vessel 110 for a specified period in step 306. During this period, the organic waste material 115 undergoes hydrolysis, wherein bacteria or other agents convert a portion of the hydrocarbon compounds in the waste material to organic acids, alcohols, and/or aldehydes. Hydrolysis of the organic waste material 115 results in the production of a liquid hydrolysis product, which flows under gravity to the unfilled region of vessel 110. The liquid hydrolysis product contains suspended and dissolved organic compounds, as well as dissolved gases. Removal of these compounds from the organic waste material during the hydrolysis process may substantially reduce emissions of ozone precursors and noxious gases produced in the subsequent composting phase. The time period during which organic waste material 115 undergoes hydrolysis will vary according to feedstock composition, temperature, and digester requirements, but will typically be on the order of three weeks. It is noted that the organic waste material may be stored within vessel 110 for a longer period of time in order to match production of the compost end product to seasonal demand.

Next, in step 308, the accumulated liquid hydrolysis product is removed from the interior of vessel 110 and transferred through conduit 124 to holding tank 130. Removal and transfer of the liquid hydrolysis product may be performed continuously, at predetermined intervals during hydrolysis, or after completion of hydrolysis. If removal and transfer of the liquids is performed intermittently, flow of the liquid from the vessel 110 interior may be started and stopped by (respectively) opening and closing a valve associated with port 202 or conduit 124. The liquid hydrolysis product is subsequently pumped into digester 140 and is incubated under anaerobic conditions to produce a biogas product and a liquid product, which may be used as an inoculant in the manner described above.

Figure 4:
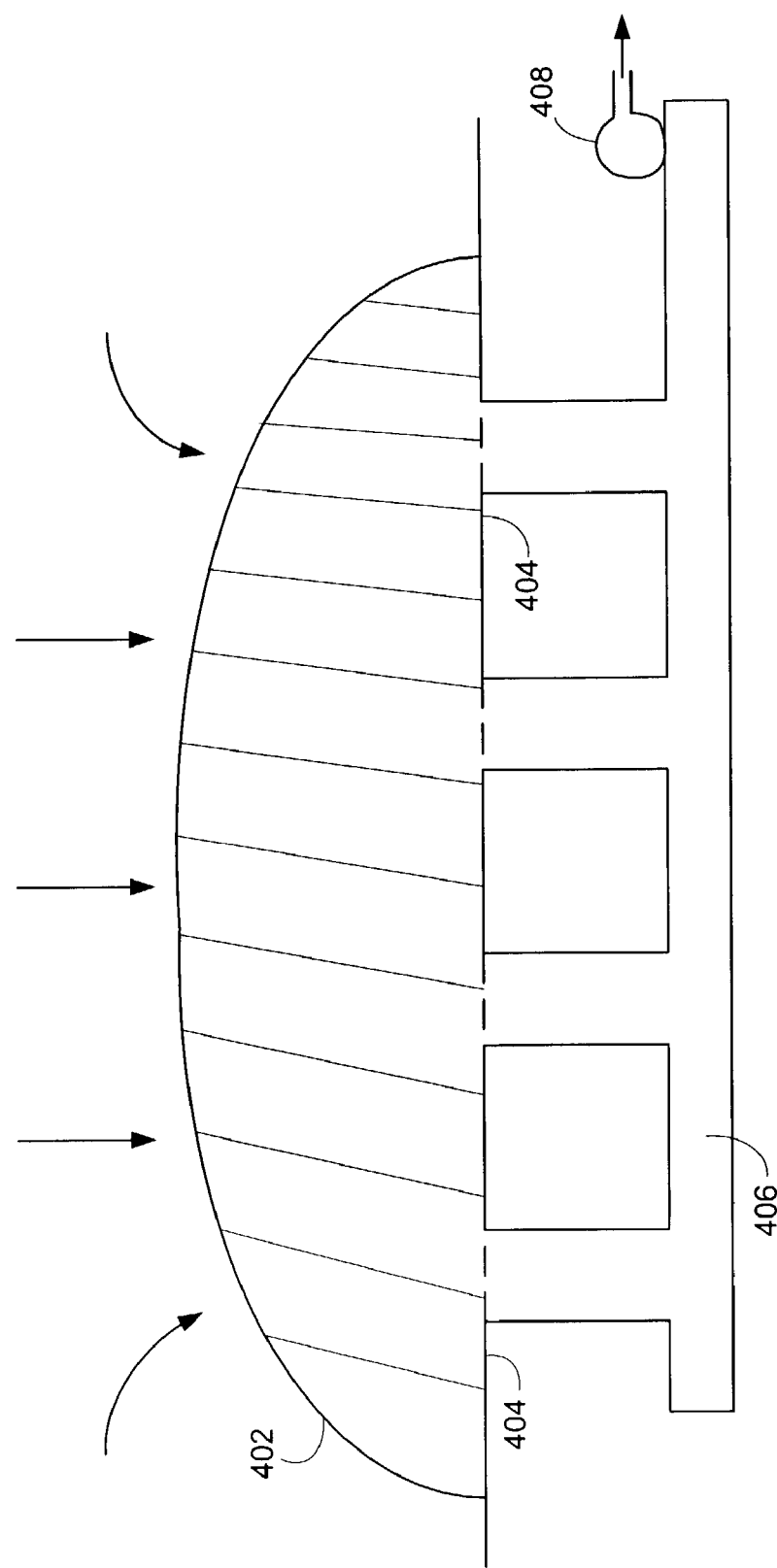
FIG. 4 is a symbolic side view of an apparatus for static reverse air composting, in accordance with a specific implementation of the invention.

In step 310, the remaining organic waste material 115 (e.g., substantially solid organic waste product) is removed from the vessel 110 and subjected to further decomposition under aerobic conditions. This step may be implemented, for example, as a static reverse air aerobic decomposition process. In this process, which is illustrated by FIG. 4, the organic waste material 115 is arranged in a pile 402 atop a supporting pad adapted with an array of air ports 404 distributed along the length and/or across the width of the pile. The outer periphery of the pile is exposed to the atmosphere. The air ports 404 communicate with at least one manifold 406. A blower 408 or similar device reduces the pressure within the manifold below the ambient pressure. The resultant pressure gradient causes ambient air adjacent to the pile to pass through the pile and into air ports 404 and manifold 406. This action provides a flow of air into the interior of the pile to facilitate aerobic decomposition reactions. The air drawn through manifold 406 is passed through a biofilter to remove any objectionable gas components prior to exhausting the air stream to the atmosphere.

Step 310 may be alternatively implemented by employing any one of a number of suitable prior art techniques, such as the forced-air composting process described in the aforementioned U.S. Pat. No. 5,461,843 or a conventional windrow-based process.

By utilizing the process discussed above, a high-quality compost may be advantageously derived from food waste and other high moisture content feedstocks while avoiding the environmental problems of traditional composting methods and the need for large capital expenditures associated with conventional hydrolysis equipment.

It should be noted that the process and system described above may be advantageously applied to a wide range of organic waste materials, including without limitation municipal solid waste (MSW), biosolids sludge, agricultural wastes, cannery wastes, manures, green and wood wastes, and other waste streams having organic content.

It will be recognized by those skilled in the art that, while the invention has been described above in terms of preferred embodiments, it is not limited thereto. Various features and aspects of the above-described invention may be used individually or jointly. Further, although the invention has been described in the context of its implementation in a particular environment and for particular applications, those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

What is claimed is:

1. A process for treating organic waste material, comprising:
    receiving the organic waste material in an elongated vessel having a longitudinal axis extending from a first portion at a first end of the vessel to a second portion at a second end of the vessel, the vessel sloped along the longitudinal axis such that the first portion is at least partially below the second portion;
    hydrolyzing the organic waste material in the vessel under anaerobic conditions to produce a liquid hydrolysis product and an organic waste product, wherein the liquid hydrolysis product separates from the organic waste product and collects at the first portion of the vessel during hydrolysis of the organic waste material; and
    decomposing the organic waste product under aerobic conditions.

2. The process of claim 1, wherein decomposing the organic waste product comprises:
    exposing the organic waste product to an ambient air environment; and
    drawing ambient air through the organic waste product to facilitate aerobic decomposition of the organic waste product.

3. The process of claim 2, wherein exposing the organic waste product to an ambient air environment comprises placing the organic waste product on a pad having a plurality of air ports in fluid communication with a manifold, and wherein drawing ambient air through the organic waste product comprises reducing pressure in the manifold to cause the ambient air to flow through the organic waste product through the air ports and into the manifold.

4. The process of claim 3, further comprising passing the ambient air in the manifold through a biofilter to filter out selected gas components from the ambient air.

5. The process of claim 1, wherein hydrolyzing the organic waste material comprises adding a liquid inoculant to the organic waste material to increase a moisture content of the organic waste material.

6. The process of claim 1, wherein a moisture content of the organic waste material is at least 60 percent.

7. The process of claim 1, wherein hydrolyzing the organic waste material comprises incubating the organic waste material.

8. The process of claim 1, wherein establishing anaerobic conditions inside the vessel comprises sealing the vessel.

9. The process of claim 8, wherein establishing anaerobic conditions inside the vessel further comprises pumping air out of the vessel after the vessel is sealed.

10. The process of claim 1, further comprising grinding the organic waste material to reduce the average particle size of the organic waste material before hydrolyzing the organic waste material.

11. The process of claim 1, wherein the liquid hydrolysis product comprises an organic acid.

12. The process of claim 1, wherein the liquid hydrolysis product comprises an alcohol.

13. The process of claim 1, wherein the liquid hydrolysis product comprises an aldehyde.

14. The process of claim 1, further comprising blending multiple waste streams of organic waste to produce the organic waste material having a selected carbon to nitrogen ratio.

15. The process of claim 1, further comprising incubating the liquid hydrolysis product in an anaerobic digester to produce a biogas and a liquid digester product.

16. The process of claim 15, wherein the liquid hydrolysis product is transferred to the anaerobic digester continuously during hydrolysis of the organic waste material.

17. The process of claim 15, wherein incubating the liquid hydrolysis product comprises combining the liquid hydrolysis product with methane producing bacteria.

18. The process of claim 15, further comprising recycling the liquid digester product by adding at least a portion of the liquid digester product to the organic waste material to increase the moisture content of the organic waste material.

19. The process of claim 15, further comprising combusting the biogas prior to release into the atmosphere.

20. The process of claim 15, wherein the biogas in liquefied to produce liquid natural gas.

21. The process of claim 1, wherein the vessel is substantially cylindrical-shaped.

22. The process of claim 1, wherein the vessel is made of a flexible polymer material.

* * * * *